US012672997B2

(12) United States Patent (10) Patent No.: US 12,672,997 B2

Oakes et al. (45) Date of Patent: Jul. 7, 2026

(54) HIGH-ACCESS PATIENT TRANSPORT SHIELD

(71) Applicant: Wisconsin Alumni Research Foundation, Madison, WI (US)

(72) Inventors: Terrence R Oakes, Middleton, WI (US); Azam Syed Ahmed, Madison, WI (US); Joseph A Kiel, Newport, MN (US); Jordan Henry, Oregon, WI (US); Andrew Culp, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1262 days.

(21) Appl. No.: 17/397,397

(22) Filed: Aug. 9, 2021

(65) Prior Publication Data

US 2022/0040020 A1 Feb. 10, 2022

Related U.S. Application Data

(60) Provisional application No. 63/063,767, filed on Aug. 10, 2020.

(51) Int. Cl.
| | |
|---|---|
| *A61G 10/00* | (2006.01) |
| *A61B 6/04* | (2006.01) |
| *A61G 10/02* | (2006.01) |

(52) U.S. Cl.
CPC ......... *A61G 10/005* (2013.01); *A61G 10/023* (2013.01); *A61B 6/0407* (2013.01); *A61G 2210/50* (2013.01)

(58) Field of Classification Search
CPC ................ A61G 10/005; A61G 10/023; A61G 2210/50; A61G 1/01; A61G 1/04; A61G 1/048; A61B 6/0407

USPC ...................................................... 600/21–22
See application file for complete search history.

(56) References Cited

U.S. PATENT DOCUMENTS

| | | | | |
|---|---|---|---|---|
| 5,950,625 | A * | 9/1999 | Bongiovanni | A61B 90/40 128/845 |
| 6,001,057 | A * | 12/1999 | Bongiovanni | A61G 10/04 5/629 |
| 6,321,764 | B1 | 11/2001 | Gauger et al. | |
| 6,461,290 | B1 | 10/2002 | Reichman et al. | |
| 6,782,571 | B1 * | 8/2004 | Josephson | A61B 6/04 5/601 |
| 7,481,234 | B1 * | 1/2009 | Gustafson | E04H 15/425 135/156 |

(Continued)

FOREIGN PATENT DOCUMENTS

| | | |
|---|---|---|
| CN | 201404402 Y | 2/2010 |
| EP | 1202696 B1 | 4/2005 |

OTHER PUBLICATIONS 3M removable repositionable double sided tapes. Parafix. Feb. 2019 (see attached) (Year: 2019).*

(Continued)

*Primary Examiner* — Sunita Reddy
(74) *Attorney, Agent, or Firm* — Boyle Fredrickson, S.C.

(57) ABSTRACT

A patient transport shield provides for a flexible support sheet supporting a patient with upstanding ribs holding a transparent cover over the patient to provide a patient volume that may hold negative pressure when the transparent cover is attached to the support sheet by a resealable pressure-sensitive attachment strip allowing rapid assembly and ready access to the patient.

19 Claims, 5 Drawing Sheets

(56) References Cited

U.S. PATENT DOCUMENTS

| | | | |
|---|---|---|---|
| 8,245,713 B2 | 8/2012 | Paschal, Jr. et al. | |
| 11,071,671 B1 * | 7/2021 | Theriault ............. | A61G 7/1025 |
| 2002/0133100 A1 * | 9/2002 | Paschal, Jr. .......... | A61G 10/005 |
| | | | 601/16 |
| 2004/0111008 A1 * | 6/2004 | Perlatti ................ | A61G 10/005 |
| | | | 600/21 |
| 2006/0247487 A1 * | 11/2006 | Arts ..................... | A61G 11/009 |
| | | | 600/21 |
| 2007/0056593 A1 * | 3/2007 | Kubicsko ............. | A61F 5/3769 |
| | | | 128/846 |
| 2008/0020695 A1 * | 1/2008 | Chang .................. | B08B 15/026 |
| | | | 55/385.2 |
| 2008/0171935 A1 * | 7/2008 | McKnight ............. | A61B 46/17 |
| | | | 5/601 |
| 2013/0220344 A1 * | 8/2013 | Shafer ................... | A61B 46/00 |
| | | | 128/855 |
| 2016/0074268 A1 * | 3/2016 | Breegi ................. | A61G 11/009 |
| | | | 600/21 |
| 2020/0179219 A1 * | 6/2020 | Petersen ............. | A61H 9/0057 |
| 2021/0307985 A1 * | 10/2021 | Staab .................. | A61G 10/005 |
| 2021/0322244 A1 * | 10/2021 | Moore ................... | E04H 15/20 |
| 2022/0001216 A1 * | 1/2022 | Adams ................ | A61G 10/023 |
| 2023/0009815 A1 * | 1/2023 | Breegi .................. | A61G 11/00 |
| 2023/0181399 A1 * | 6/2023 | De Man ................ | A61G 10/02 |
| | | | 600/21 |

OTHER PUBLICATIONS

Amel Amalou Ma et al; Disposable Isolation Device to Reduce COVID-19 Contamination during CT scanning; 2020 Published by Elsevier Inc. on behalf of the Association of University Radiologists; https://doi.org/10.1016/j.acra.2020.05.017; pp. 1-17.

* cited by examiner

HIGH-ACCESS PATIENT TRANSPORT SHIELD

CROSS REFERENCE TO RELATED APPLICATION

This application claims the benefit of U.S. provisional application 63/063,767 filed Aug. 10, 2020 and hereby incorporated by reference.

STATEMENT REGARDING FEDERALLY SPONSORED RESEARCH OR DEVELOPMENT

--

BACKGROUND OF THE INVENTION

The present invention relates generally to medical drapes for preventing the transfer of infectious agents from a patient and in particular to a drape system suitable for use for transporting patients and for use in radiological scanners.

Negative pressure ventilation in hospital rooms can be used to limit the transmission of infectious agents from patients to hospital personnel and the environment. This protection, however, is lost when a patient needs to be transported through hospital hallways and elevators. Imaging suites holding radiological scanners such as CT, MRI, or PET machines may also be equipped with negative pressure ventilation. While this provides protection similar to a negative pressure hospital room, the need for such imaging suites to receive new patients throughout the day requires that, after the scanning of a patient having an infectious disease, the imaging suite be shut down for a period of time sufficient to allow multiple cycles of complete air exchange. The scanner must also be subject to a thorough cleaning. Together the shutdown and cleaning can take more than an hour, reducing the availability of the scanning equipment and increasing medical costs.

SUMMARY OF THE INVENTION

The present invention provides a low-cost patient shield that can enclose the patient for transport through the hospital environment and during the scanning process. A simple, resealable pressure-sensitive strip assembles a base sheet and covering drape allowing rapid deployment of the shield and improved rapid access to the patient when required.

More specifically, in one embodiment, the invention provides a flexible support sheet sized to receive a recumbent patient thereupon within a support sheet periphery. A set of flexible ribs is positionable in an assembled state on the flexible support sheet to extend upward and over the flexible support sheet, and a transparent barrier sheet is sized to cover the flexible ribs in the assembled state and to extend downward to the support the sheet periphery, the transparent barrier sheet together with the flexible support sheet defining a volume surrounding the recumbent patient. A resealable pressure-sensitive strip sealingly connects the support sheet periphery to the transparent barrier sheet.

It is thus a feature of at least one embodiment of the invention to provide a simple patient transport shield offering rapid and general access to the patient by unsealing a resealable pressure-sensitive strip that is also used to fabricate the patient transport shield.

In one embodiment, the resealable pressure-sensitive strip may be an adhesive material. This adhesive material may be attached, for example, between the flexible support sheet and transparent barrier sheet and covered on one side with a release liner removable to reveal the pressure-sensitive adhesive. In one embodiment the resealable pressure-sensitive strip may be on a double-sided tape having a permanent pressure-sensitive adhesive on one side and a releasable pressure-sensitive adhesive on the other side.

It is thus a feature of at least one embodiment of the invention to provide a simple and low cost assembly method that can flexibly accommodate a high degree of patient access, IV lines, electrical leads and the like. One feature of at least one embodiment of the invention is to make use of readily available commercial components such as double stick tape to provide a low-cost assembly method allowing the shield to be freely used and then disposed of to reduce infection transfer.

In an alternative embodiment, the resealable pressure-sensitive strip is a hook and loop fastener material.

It is thus a feature of at least one embodiment of the invention to also provide a longer-term solution that can accommodate multiple resealing operations.

The patient transport shield may include a vacuum line attachment and the ribs may support the transparent barrier sheet away from the flexible support sheet under negative pressure.

It is thus a feature of at least one embodiment of the invention to permit effective isolation of infectious agents within the patient transport shield through negative pressure.

The patient transport shield may further include an air filter positioned in at least one of the flexible support sheet and transparent barrier sheet near a head location of the recumbent patient for the inflow of filtered air into the volume.

It is thus a feature of at least one embodiment of the invention to provide a controlled inlet of fresh air consistent with maintaining a negative pressure and adequate patient oxygen.

The flexible support sheet may provide a set of loop handles at its laterally opposed edges and may be adapted to support a patient when the flexible support sheet is suspended by the handles.

It is thus a feature of at least one embodiment of the invention to provide a patient transfer shield permitting rapid transfer of the patient from a gurney to a radiological scanning table and the like without breaching the shield around the patient.

The flexible support sheet, flexible ribs, transparent barrier sheet, and resealable pressure-sensitive strip may be free from metal and substantially radiolucent.

It is thus a feature of at least one embodiment of the invention to provide a shield that encloses the patient during an entire time from transport from the patient's room to a radiological scanner and back without removing of the patient.

The flexible support sheet, flexible ribs, and transparent barrier sheet are adapted to assemble together into a structure fitting within a cylinder defined by the bore of standard imaging equipment (CT, PET, MRI) typically having at least a 18 inch diameter.

It is thus a feature of at least one embodiment of the invention to provide a shield fully compatible with most radiological scanners.

The ribs may be selected from the group consisting of thermoplastic battens, thermoplastic pipes, and inflatable tubular sleeves of flexible thermoplastic sheeting.

It is thus a feature of at least one embodiment of the invention to provide a generally flexible structure that will bend or flex out of the way when brushing against the bore of the radiological scanner.

In one embodiment, the flexible support sheet may provide a series of tubular chambers and an inflation valve to inflate the tubular chambers to provide a cushioning under a patient resting on the flexible support sheet.

It is thus a feature of at least one embodiment of the invention to provide improved patient comfort while maintaining radiolucency and flexibility.

The ribs may be substantially flat in a relaxed state and are flexed to install on the flexible support sheet to extend in an arch upward from the flexible support sheet and laterally across the flexible support sheet with ends of the arches attach to edges of the flexible support sheet.

It is thus a feature of at least one embodiment of the invention to provide a practical disposable patient shield that can be stored flat or in a roll in quantity at a healthcare site.

The patient transport shield may further include stabilizer legs fixable to ribs of the set of flexible ribs to extend along an upper surface of the flexible support sheet stabilizing the upward angle of the rib with respect to the support sheet.

It is thus a feature of at least one embodiment of the invention to provide a simple structure that can resist longitudinally inward forces caused by negative pressures pulling on the transparent barrier sheet.

The patient transport shield may include pairs of arched ribs attached to each other over the flexible support sheet as they cross.

It is thus a feature of at least one embodiment of the invention to provide a structural resistance to longitudinal and transverse inward forces caused by negative pressure.

In one embodiment, the transparent barrier sheet may provide a central arched portion attached to arch-shaped end panels to provide a downwardly concave cover terminating at a horizontally outwardly extendable skirt portion that may abut an upper surface of the flexible support sheet as sealed to the upper surface of the flexible support sheet with the resealable pressure-sensitive strip.

It is thus a feature of at least one embodiment of the invention to provide both rapid assembly and good air sealing through a tailoring of the transparent barrier sheet to the rib design.

These particular objects and advantages may apply to only some embodiments falling within the claims and thus do not define the scope of the invention.

DETAILED DESCRIPTION OF THE PREFERRED EMBODIMENT

Figures 1, 2, 3:
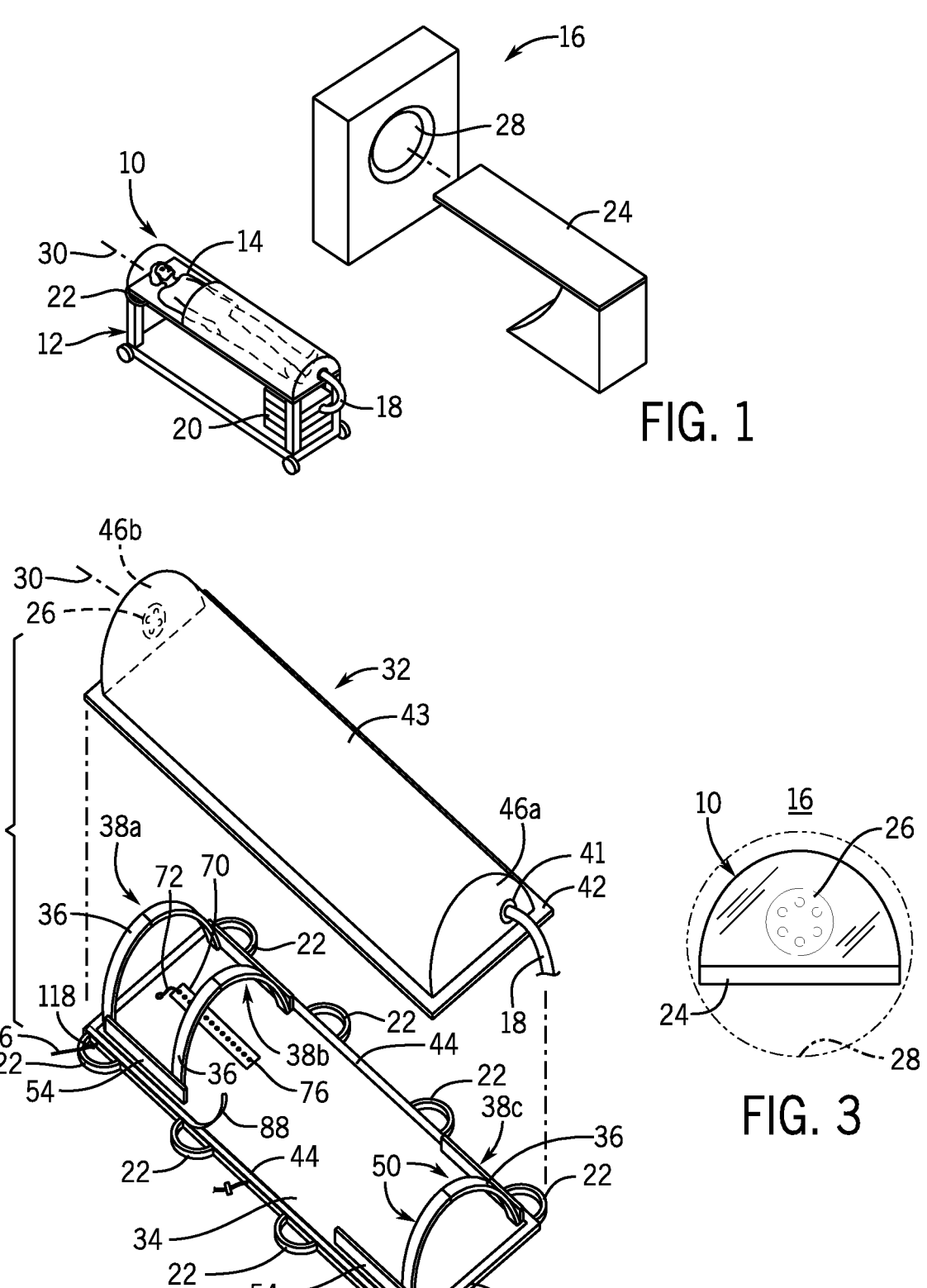
FIG. 1 is a simplified depiction of a radiological scanner adjacent to a patient gantry such as may hold the patient transport shield of the present invention and allow transfer to the scanner table while the patient is within the transport shield.
FIG. 2 is an exploded perspective view of the patient support shield of FIG. 1 in a first embodiment using laterally extending arched ribs and a transparent cover fitted from multiple elements.
FIG. 3 is an end elevational view of the assembled patient transport shield of FIG. 2 within a circle defining a bore diameter of the radiological scanner of FIG. 1.

Referring now to FIGS. 1 and 2, the present invention provides a patient transport shield 10, for example, that can fit on a patient gurney 12 for transport of a recumbent patient 14 within the hospital through the halls, elevators, and the like to a radiological scanner 16 such as a PET machine, CT machine, or MRI machine.

During the transport, the patient gurney 12 may provide for airflow to the patient 14 through the otherwise airtight patient transport shield 10 surrounding the patient 14 by means of a vacuum line connection 41 and filter 26. The vacuum line connection 41 may attach to a vacuum line 18 communicating with a pump 20 that serves to pump air from the volume of the airtight patient transport shield 10 to create a negative pressure within an envelope of the patient transport shield 10. This negative pressure encourages fresh air to be drawn into that envelope through a filter 26 positioned near the patient's head. Desirably, the pump 20 will provide a filtered outlet into the environment using, for example, a hospital grade HEPA or an N95 filter and will provide an airflow consistent with the volumes and rates provided by hospital vacuum systems of approximately 3 to 4 standard cubic feet per minute. The filter 26 providing fresh air may also be a hospital grade HEPA or an N95 filtration system and will constrain the inflow of air to provide a slight negative pressure within the volume so that minor leaks in the patient transport shield 10 produce inward airflow.

The patient transport shield 10 may have side handles 22 to function in the manner of a patient transfer sheet allowing the patient 14 to be lifted from the patient gurney 12 by the handles 22 for transfer to the radiological scanner table 24 for scanning and then back again to the patient gurney 12 after the scan is complete.

Referring now to FIG. 2, the patient transport shield 10 may provide a flexible, generally rectangular support sheet 34 on which the patient 14 (not shown in FIG. 2) may lie. This support sheet 34 is sized to be larger than the outline of the patient 14 in both the longitudinal direction along axis 30 and perpendicularly in a transverse direction with the inferior/superior axis of the patient 14 aligned with the longitudinal direction 30.

The rectangular support sheet 34 holding the patient 14 as so positioned may then be covered by an upper transparent barrier sheet 32 positioned above a support sheet 34 and spaced from the support sheet 34 by a set of ribs 36 extending upward from edges of the support sheet 34 and over the patient 14 on the support sheet 34 to define an enclosed patient volume therebetween. The upper transparent barrier sheet 32 may be a transparent polymer film that blocks air and water flow, albeit the invention contemplates that a combination of transparent and opaque materials may be used including filter type material preventing the transfer of pathogens but allowing air transfer.

The support sheet 34, for example, may be a fiber reinforced polymer material providing an airtight and watertight surface sufficiently strong to allow the patient 14 to be lifted and supported by the support sheet 34 by healthcare professionals holding the handles 22 horizontally outwardly from the transverse edges of the support sheet 34.

Referring still to FIG. 2, in one embodiment, the ribs 36 may be thin, flexible polymer strips or battens designed to be radiolucent with respect to imaging x-rays and to, respectively, flex resiliently into three arches 38a-38c having transversely opposed ends attached near opposite transverse edges of the support sheet 34. The arches 38 are distributed longitudinally at the longitudinal ends of the support sheet 34 near the patient's head and feet (arches 38a and 38b, respectively), and approximately one third of the longitudinal dimension of the support sheet 34 is spaced in an inferior direction from the end of the patient support sheet 34 closest to the patient's head. This arch 38b provides extra support for spacing the transparent barrier sheet 32 away from the patient's head region. The attachment of the arches 38 to the support sheet 34 may be, for example, by means of a pressure-sensitive adhesive (e.g., double stick tape) or by molded features or snaps incorporated into one or both of the upper surface of the support sheet 34 and the ends of the legs of the arches 38, or by other attachment means generally understood in the art.

Referring now also to FIG. 3, the patient transport shield 10 as assembled together around the patient is desirably sized to fit within the bore 28 of a standard radiological scanner. In this respect, the patient transport shield 10 will fit within a cylinder having a diameter of 22 inches such that a longitudinal axis 30 of the patient transport shield aligns with the axis of this cylinder. As such, the height of the arches 38 vertically measured from a horizontal plane of the support sheet 34 will be less than the distance from the upper surface of the table 24 to the peak of the bore 28. The specific dimensions may be adjusted to account for varying sizes of specific radiological machines.

Referring still to FIG. 2, in one embodiment, the transparent barrier sheet 32 may be assembled from multiple flexible, transparent sheet components to closely conform to the shape of the ribs 36. In this regard, the transparent barrier sheet 32 may provide a skirt 42 extending outward like a rectangular frame to a periphery that matches the periphery of the support sheet 34. The underside of this skirt 42 may be sealingly attached to the periphery of the support sheet 34 by a releasable pressure-sensitive attachment strip 44 running around the periphery of the support sheet 34 just inside of that periphery and outside of the upwardly extending ribs 36. This releasable pressure-sensitive attachment strip 44 will be discussed in more detail below, but generally will run a full length of one or both longitudinal edges of the patient transport shield and desirably for a significant portion of at least 50% of this length, continuously or intermittently, possibly located around the head and torso of the patient 14 to provide extremely high degree of accessibility to the patient.

The inside of the transversely opposed edges of the frame of the skirt 42 join to an upwardly arching cover portion 43 formed in an elastic catenary shape provided by the flexible ribs 36 to conform to and be supported by the ribs 36 which support it. End panels 46a and 46 having a periphery conforming to the elastic catenary shape may be attached at either ends of the cover portion 43 and sealed to those ends, for example, by heat or ultrasonic welding. Lower edges of the end panels 46 attach to inner edges of the longitudinally opposed skirt 42 to complete a substantially continuous downwardly open and concave trough form.

The filter 26 may be placed in one end panel 46b, and the opposed end panel 46a may provide attachment 41 for the vacuum line 18, for example, surrounded by a strain relief to resist tearing of the sheet material.

The thus formed structure of the transparent barrier sheet 32 may be easily collapsed and folded for transport or storage and quickly assembled and sealed to the support sheet 34 by the releasable pressure-sensitive attachment strip 44. In some embodiments, the releasable pressure-sensitive attachment strip 44 may also be placed along the outer periphery of the ribs 36. For ease of assembly of the patient transport shield 10, the skirt 42 on one laterally extending side may be pre-attached to the support sheet 34.

Figures 4, 5, 6, 7:
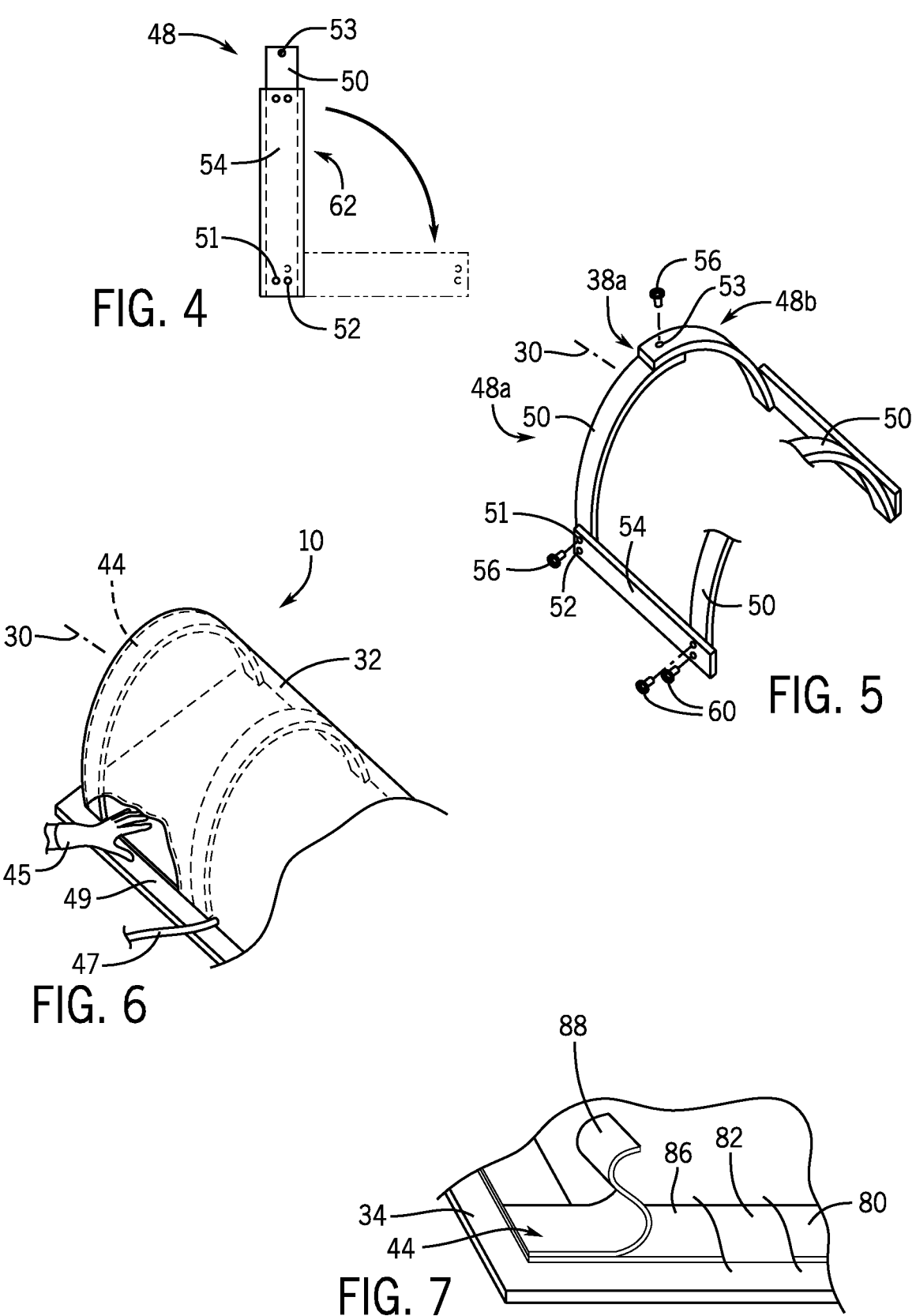
FIG. 4 is a side elevational view of a rib component used in the embodiment of FIG. 2 before deployment of a stabilizer leg.
FIG. 5 is a perspective fragmentary view of a rib assembled from two rib components of FIG. 4.
FIG. 6 is a fragmentary perspective view of the assembled patient transport shield of FIG. 2 showing access to the patient by separation of the transparent cover material from the flexible support sheet at a resealable pressure-sensitive attachment strip.
FIG. 7 is a detailed fragmentary view of a corner of the flexible support sheet showing the use of a double stick tape material in one embodiment for providing the pressure-sensitive attachment.

Referring now to FIGS. 2, 4 and 5, in this embodiment, each rib 36 may be assembled from two battens 48a and 48b, the latter providing a flexible arch half 50 constructed, for example, of a 1/16 inch thick polymer material attached by a plastic rivet 52 to a polymer stabilizer bar 54 at a lower end. Flexible arch half 50 and stabilizer bar 54 may be folded as depicted by FIG. 4 into alignment for shipping, and then the stabilizer bar 54 may be folded 90° downwardly from the flexible arch half 50 and held in this position by insertion of a snap pin 56 through second holes 51 now aligned between the flexible arch half 50 and stabilizer bar 54.

Referring now also to FIG. 5, the end of the flexible arch half 50 not connected to the stabilizer bar 54 may include a hole 53 for attaching it via an additional snap pin 56 to a corresponding end of a second batten 48b to complete the arch 38a. A second flexible arch half 50 may then be assembled in a similar manner to form a second arch 38b which may be attached to the second end of the stabilizer bars 54 attached to the arch 38a with two spaced apart plastic snap pins 60 to provide ribs 36 that can support the transparent barrier sheet 32 and be resistant to some longitudinal forces of that transparent barrier sheet caused by negative pressure. An adhesive 62, such as a pressure-sensitive double stick tape may be attached to the underside of the stabilizer bars 54 as so positioned to attach them to the upper surface of the support sheet 34. The remaining arch 38c may be constructed in similar form including arch halves 50 and stabilizer bars 54 to be positioned in mirror opposition to arch 38a. A pressure-sensitive adhesive may be used together or in lieu of the pins 60 and 56 in some embodiments.

The support sheet 34 may include a tear strip 70 centered near the position of the patient's head on the support sheet 34. The tear strip 70 may cover a slot for receiving a head coil of an MRI machine into the volume of the patient transport shield 10 but may include a string 72 that may be pulled to tear a paper tape along a slot line 76 opening this slot as needed and otherwise providing a hermetic seal against contamination passing through the support sheet 34.

Referring now to FIG. 6, the releasable pressure-sensitive attachment strip 44 allows the transparent barrier sheet 32 to be sealed against the support sheet 34 during use but at any time lifted for rapid access to the patient 14 eliminating the need for glovebox type arrangements that can be difficult to use and limiting of such access. In this regard, a healthcare professional's hand 45 may fit underneath a lifted flap of the transparent barrier sheet 32 in a way that minimizes the opening size to provide continued containment of pathogens. This minimization is facilitated by the ability to make the opening in any location along the longitudinal edges of the patient transport shield 10 close to any region that needs access and by the ability of the healthcare professional to keep the transparent barrier sheet against his or her hand viewing any procedure through that sheet.

The attachment of the transparent barrier sheet 32 to the support sheet 34 using a releasable pressure-sensitive attachment strip 44 readily accommodates insertion of IV lines 47 or electrical leads or the like through the patient transport shield 10 with no or small gaps that can be accommodated by the vacuum pump 20 providing intake air blocking the escape of infectious agents.

After access to the patient 14 has been provided in this manner, the lifted edge may be resealed against the releasable pressure-sensitive attachment strip 44.

Referring now to FIG. 7, in one embodiment the releasable pressure-sensitive attachment strip 44 may be a double-sided tape having a lower permanent pressure-sensitive adhesive 80 permanently joining a carrier tape strip 82 positioned on top of the adhesive 80 to the support sheet 34. A removable or releasable pressure-sensitive adhesive 84 on top of the carrier tape strip 82 is then exposed upwardly to attach the support sheet 34 to the transparent barrier sheet 32 as described above. A siliconized release liner 88 covers releasable pressure-sensitive adhesive 86 before use to preserve the adhesive nature of the pressure-sensitive adhesive 86 during transportation and shipping. Double-sided tape suitable for this purpose is widely available from a number of commercial suppliers including Uline of Wisconsin, United States, under the trade designation "removable" providing one side with a permanent adhesive and one side with a repositionable adhesive, for example, under the trade designations S-15719.

Figures 8, 9, 10, 11:
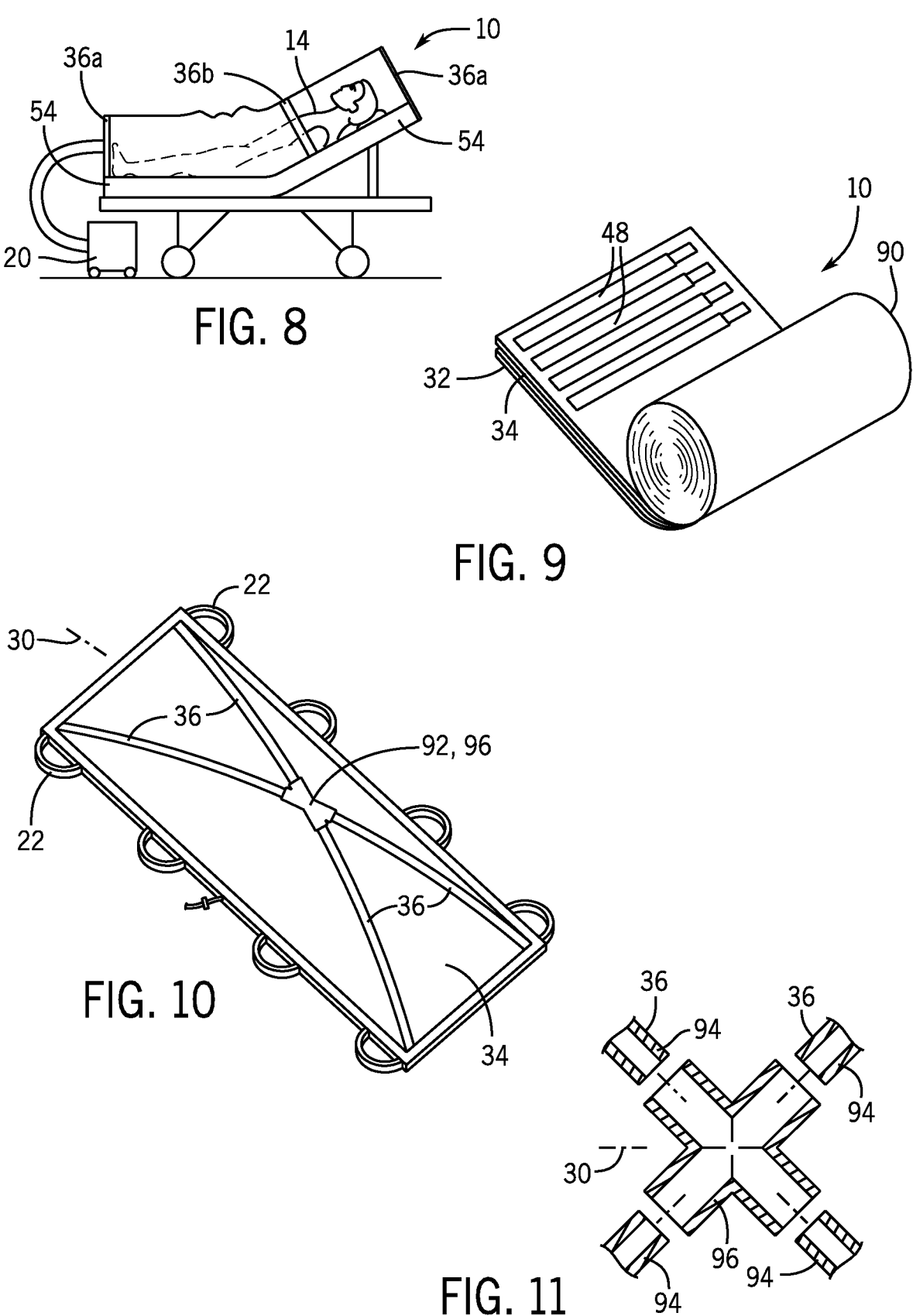
FIG. 8 is a simplified elevational side view of a patient within the patient transport shield on a hospital bed showing an ability of the patient transport shield to conform to bed articulations.
FIG. 9 is a perspective view of the patient transport system of FIG. 2 in a collapsed form to be rolled up for storage.
FIG. 10 is a perspective view of an alternative embodiment of the flexible support sheet and flexible ribs providing X-bracing for longitudinal and lateral stability.
FIG. 11 is a cross-sectional view of connector assembling of the ribs of FIG. 10 in X-bracing

Referring now to FIG. 9, the flexibility of the support sheet 34 and the arrangement of the ribs 36 and stabilizer bars 54 toward the longitudinal ends of the patient transport shield 10 provide longitudinal flexibility in the patient transport shield 10, for example, allowing the patient 14 to be placed on an articulated hospital bed or gurney with his or her head elevated. In this arrangement, the patient transport shield 10 will fold in slightly at its middle while preserving the volume around the patient's head so that the patient 14 may remain comfortable while waiting for a procedure.

Referring now to FIGS. 1 and 9, the patient transport shield 10 may be stored and/or shipped in a compact form with the transparent barrier sheet 32 collapsed by folding the end panels 46a and 46b inwardly and downwardly and placing the flattened transparent barrier sheet 32 under the support sheet 34 to be rolled together into a tight roll 90, for example, to be stored in a box or the like. The battens 48 assembled from subcomponents may have a disassembled total length to fit and be stored inside this roll arranged generally along the axis of the rolled cylinder.

Referring now to FIGS. 10 and 11, in an alternative construction two ribs 36 may be arranged in an X-configuration, each rib 36 arching upward from a first corner of the support sheet 34 at one longitudinal end of the support sheet 34 and then arching downward to a second corner of the support sheet 34 diagonally opposite from the first corner, the two ribs 36 crossing at a center connector 92 over the support sheet 34. This X-configuration provide a cross bracing eliminating the need for stabilizer bars 54 and able to resist longitudinal and transverse forces. In this embodiment, the ribs 36 may be flexible polymer tubes 94 inserted into a four-way connector 96 and held by press fit for rapid assembly. Pockets in support sheet 34 or molded connectors may be used to attach ends of the tubes 94 forming the ribs 36 to the support sheet 34.

Figure 12:
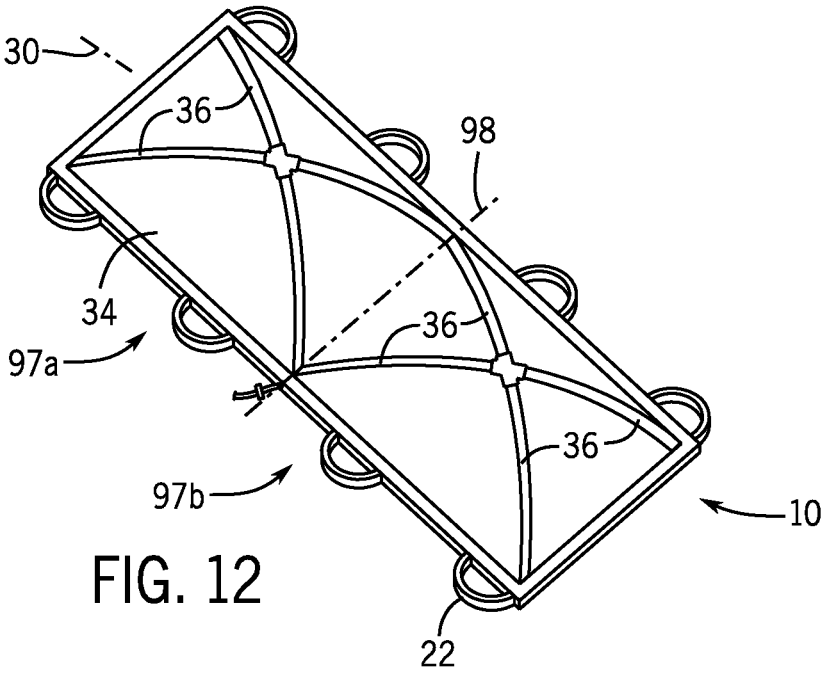
FIG. 12 is a figure similar to that of FIG. 10 showing the X-bracing divided into two portions to improve flexibility of the patient transport shield along the longitudinal axis and to reduce rib storage size.

Referring now to FIG. 12, improved longitudinal bending of the patient transport shield 10 as described with respect to FIG. 8 may be provided by breaking ribs 36 in the X-configuration into two separate X-configurations for upper and lower longitudinally arrayed portions 97a and 97b of the support sheet 34. Each portion 97 will then have separate pairs of ribs 36 in the X-configuration, the ribs 36 of each pair proceeding from corners of the support sheet 34 in that portion 97 to opposite transverse sides of a midline 98 extending transversely across the center of the support sheet 34. The construction of each of these pairs of ribs 36 is otherwise similar to that of FIG. 10.

Figure 13:
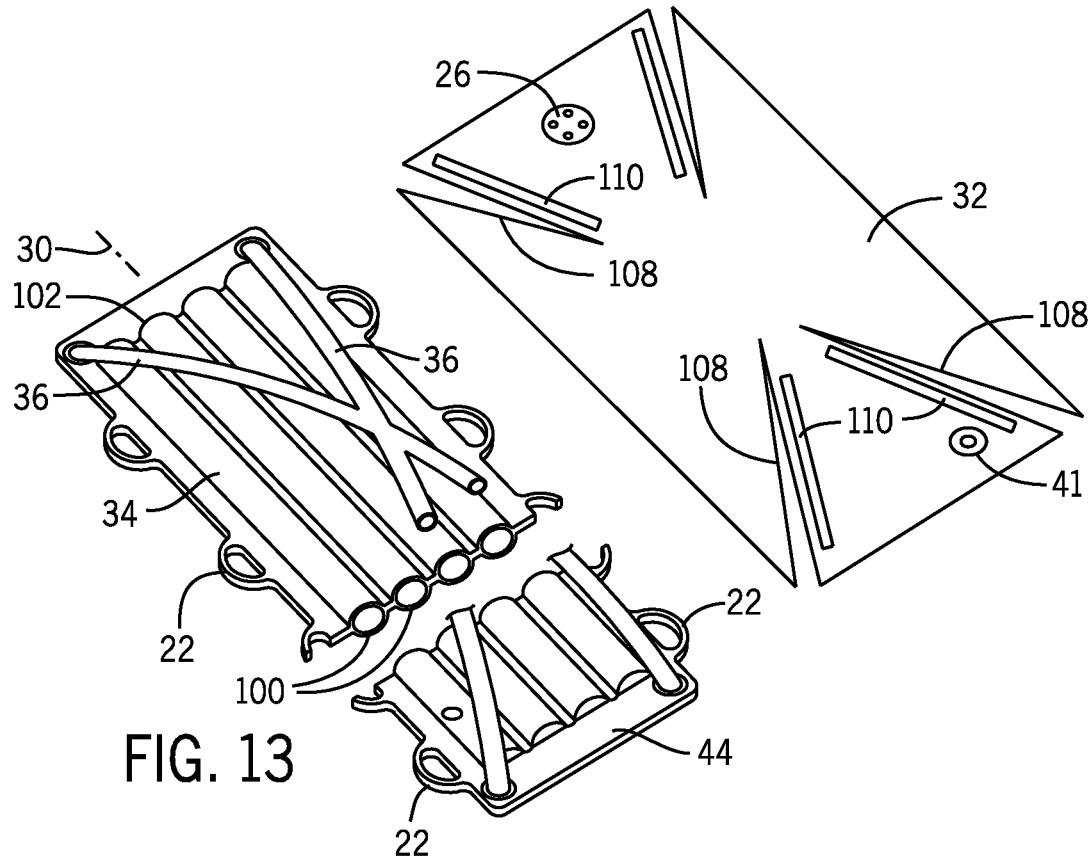
FIG. 13 is a figure similar to that of FIG. 12 showing an alternate embodiment in which the ribs are inflated and part of an inflatable patient support mattress forming the flexible support sheet and further showing a simplified upper transparent barrier sheet that may be fabricated on site.

Referring now to FIG. 13, this X-configuration structure may be extended to provide for inflatable ribs 36, for example, formed of tubes of a flexible polymer material providing stiffness when inflated. Here, as with the case in the embodiment of FIG. 10, the ribs 36 may extend to opposite corners of the support sheet 34; however, the longitudinal compressibility of the tubes can permit additional flexibility, for example, as shown in FIG. 8. In this embodiment, each of the inflatable ribs 36 may communicate with additional mattress tubes 100 extending along the plane of the support sheet 34 (and formed in part from material of the support sheet 34) in the matter of an air mattress, these mattress tubes 100 having interior cavities that may be given a mattress-like quality by inflation. Intercommunication between the mattress tubes 100 and the inflatable ribs 36 allows the entire structure to be rapidly inflated from a single inflation point 102, for example, using a pressurized gas cartridge. Note that the inflatable ribs 36 may be provided even without the additional mattress tubes 100, allowing faster inflation and simpler lower-cost construction.

In this embodiment and those shown in FIGS. 10 and 12, the transparent barrier sheet 32 may be cut from a sheet of material having darts 108 generally aligned with the ribs 36 that can be assembled, for example, by a pressure-sensitive attachment strip 110 along one edge of each dart to provide a conforming cover to the ribs 36 and support sheet 34 that is assembled on site and can roll or fold more compactly prior to assembly.

Figure 14:
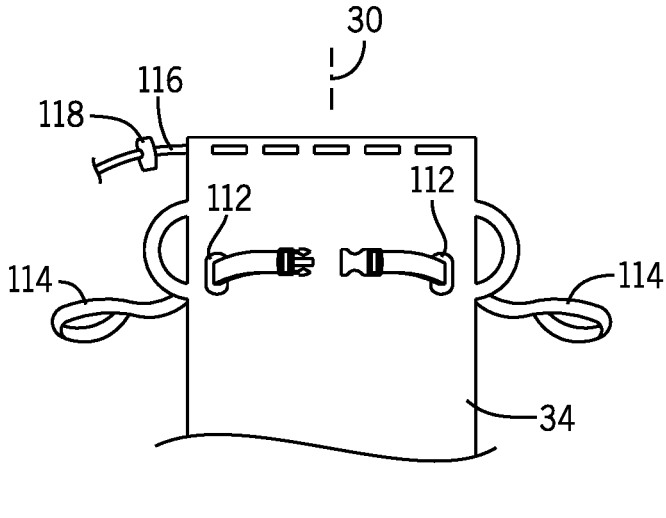
FIG. 14 is a top plan fragmentary view of one end of the support sheet of FIG. 2 showing patient support straps and a cinch strip for reducing the width of the flexible support sheet for transport on a gantry.

Referring now to FIG. 14, in some embodiments, the support sheet 34 may include passageways 112 for patient restraint belts 114 that may be placed over the patient on the support sheet 34 and extend through the support sheet to attach to a patient bed or gurney or the like. The restraint belt may be either a standard component of a gurney or scanner bed, thus extending between the support sheet and clear cover and over the patient, or a belt may be attached to the support sheet and extended over the patient, with couplers to attach the support sheet to the standard bed belt attachment points.

The support sheet 34 may provide for cinch lines 116 extending at multiple locations separated longitudinally and extending transversely across the support sheet 34. The cinch lines 116 may be threaded in the serpentine fashion through the material of the support sheet 34 so that the cinch lines 116 may be pulled to compress the lateral distance of the support sheet 34, for example, when moving the patient transport shield 10 from a bed to a gurney having a narrower width. The cinching may be retained by spring-loaded cinch clamp 118 of a type generally well known in the art.

Figure 15:
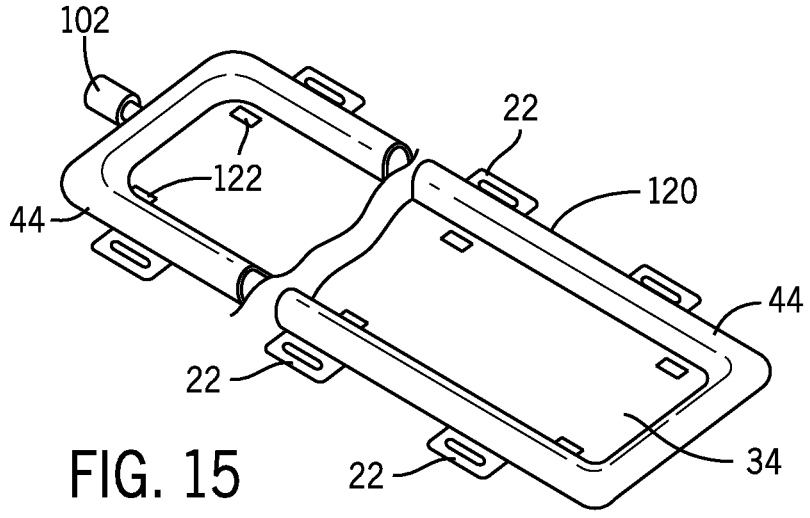
FIG. 15 is a figure similar to that of FIG. 13 showing an alternative embodiment where the inflatable tubes on the support sheet provide a simple protective periphery.

Referring now to FIG. 15, in one embodiment, the support sheet 34, similar to that described above with respect to FIG. 2, may attach and be extended by an inflatable tube 120 passing around its periphery. This inflatable tube 120 may be inflated at inflation point 102, for example, being a valve or a canister of gas as discussed above. The inflatable tube 120, when inflated, provides a bumper surrounding and centering the patient (not shown) on the sheet 34 and offering an elevated position for attachment to the pressure sensitive adhesive strip 44. The ribs 36 (not shown in FIG. 15) may be inflatable as shown in FIG. 13 attaching to the inflatable tube 120 and communicating therewith, or may be flexible resilient ribs 36 as shown in FIG. 2, for example, received within molded sockets 122 attached to the sheet 34, or, for example, receiving ends of the tubes ribs 36 shown in FIG. 10 or 12.

Another embodiment encompasses the torso and head, or head alone, with a correspondingly smaller size, fewer materials, and perhaps fewer support structures. The general design and components are otherwise similar as described elsewhere here. This embodiment may provide better access to the patient's lower body while still providing adequate control of the patient's respiratory environment. This embodiment may also be easier to install and remove over a supine patient, or for an unresponsive, inactive, or unco-operative patient.

It is believed that those of ordinary skill in the art in the context of the invention will understand that a repositionable or releasable adhesive will allow separation and reattach-ment for sealing of 2 to 3 times and those that are permanent will cause damage to the materials when disassembled after 30 minutes of attachment. More generally, it is generally recognized that pressure-sensitive adhesives may be catego-rized as follows:

| Pressure-sensitive adhesive type | Peel strength in grams/25 mm | Loop tack in grams per 25 mm | Shear |
|---|---|---|---|
| Permanent | >2000 | 1400 | High |
| Removable | 250-275 | 400 | Medium |
| Repositionable | 90-100 | 250 | Low |

In this regard, the present invention contemplates the use of a removable or repositionable adhesive to releasably attach to the transparent barrier sheet 32 and generally an adhesive having a peel strength per the above table of less than 500 and preferably less than 300 or 275 g/25 mm.

Desirably all of the materials of the patient transport shield 10 are fully compatible with radiological scanners such as MRI, PET and CT. In this regard they may be constructed without any electrically conductive material that would support eddy currents in MRI devices and are free from magnetic materials for the same reason. Generally, the patient transport shield 10 will exclude metal materials. In addition, materials are desirably radiolucent, for example, having a radiological absorption equivalent to less than 1 cm of distilled water.

While the present invention has been described with respect to negative pressure, it will be appreciated that the vacuum system may be swapped for a pressurization system for example to provide a positive pressure for immune compromised patients.

Certain terminology is used herein for purposes of refer-ence only, and thus is not intended to be limiting. For example, terms such as "upper", "lower", "above", and "below" refer to directions in the drawings to which refer-ence is made. Terms such as "front", "back", "rear", "bot-tom" and "side", describe the orientation of portions of the component within a consistent but arbitrary frame of refer-ence which is made clear by reference to the text and the associated drawings describing the component under dis-cussion. Such terminology may include the words specifi-cally mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "com-prising", "including" and "having" are intended to be inclu-sive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties To aid the Patent Office and any readers of any patent issued on this application in interpreting the claims appended hereto, applicants wish to note that they do not intend any of the appended claims or claim elements to invoke 35 U.S.C. 112(f) unless the words "means for" or "step for" are explicitly used in the particular claim.

What we claim is:

1. A patient transport shield comprising:
   a flexible support sheet sized to receive a recumbent patient thereupon within a support sheet periphery;
   a set of flexible ribs positionable in an assembled state on the flexible support sheet to extend upward and over the flexible support sheet and wherein at least one of the set of flexible ribs is positioned longitudinally on the flexible support sheet between the head of the patient and the feet of the patient;

a transparent barrier sheet sized to cover the flexible ribs in the assembled state and to extend downward to the support sheet periphery and together with the flexible support sheet to define an enclosed volume surrounding the entire recumbent patient;

a resealable pressure-sensitive strip sealingly connecting the support sheet periphery to the transparent barrier sheet; and wherein each rib of the set of flexible ribs is formed of elongate members having an outer periphery configured to flex between a straightened configuration and an arc conforming to a curvature of the transparent barrier sheet while the transparent barrier sheet is supported away from the patient on the outer periphery; and wherein the set of flexible ribs operatively couple to an inflatable tube surrounding a periphery of the support sheet configured to provide a bumper surrounding and centering the patient on the support sheet.

2. The patient transport shield of claim 1, wherein the resealable pressure-sensitive strip is an adhesive material.

3. The patient transport shield of claim 2, wherein the adhesive material is attached at one side to at least one of the flexible support sheet and transparent barrier sheet and covered on another side with a release liner removable to reveal the adhesive material.

4. The patient transport shield of claim 3, wherein the resealable pressure-sensitive strip is a double-sided tape having a permanent pressure-sensitive adhesive on one side and a releasable pressure-sensitive adhesive on the other side.

5. The patient transport shield of claim 1, wherein the resealable pressure-sensitive strip is a hook and loop fastener material.

6. The patient transport shield of claim 1 further including a vacuum line attachment for releasable attachment to a vacuum system and wherein the set of flexible ribs support the transparent barrier sheet away from the flexible support sheet under negative pressure.

7. The patient transport shield of claim 6 further including an air filter positioned in at least one of the flexible support sheet and transparent barrier sheet providing for inflow of filtered air into the volume.

8. The patient transport shield of claim 1, wherein the flexible support sheet provides a set of loop handles at its laterally opposed edges and wherein the flexible support sheet is arranged to support a patient from the set of loop handles.

9. The patient transport shield of claim 1, wherein the flexible support sheet, the set of flexible ribs, the transparent barrier sheet, and the resealable pressure-sensitive strip are free from metal, and radiolucent to x-rays.

10. The patient transport shield of claim 1, wherein the flexible support sheet, the flexible ribs, and the transparent barrier sheet are configured to assemble together into a structure fitting within a cylindrical volume with an 18-inch diameter.

11. The patient transport shield of claim 1, wherein the set of flexible ribs are selected from the group consisting of thermoplastic battens, thermoplastic pipes, inflatable tubular sleeves of flexible thermoplastic sheeting.

12. The patient transport shield of claim 1, wherein the flexible support sheet provides a series of tubular chambers and an inflation valve to inflate the tubular chambers to provide a cushioning under a patient resting on the flexible support sheet.

13. The patient transport shield of claim 1, wherein the inflatable tube provides a perimeter tubular chamber surrounding the flexible support sheet supporting the patient and wherein the resealable pressure-sensitive strip is attached to an upper surface of the perimeter tubular chamber above the flexible sheet while the perimeter tubular chamber is inflated.

14. The patient transport shield of claim 1, wherein the transparent barrier sheet provides a central arched portion attached to arch-shaped end panels to provide a downwardly concave cover terminating at a horizontally outwardly extendable skirt portion that is configured to abut an upper surface of the flexible support sheet as sealed to the upper surface of the flexible support sheet with the resealable pressure-sensitive strip.

15. The patient transport shield of claim 14 further including stabilizer legs fixable to respective rib of the set of flexible ribs to extend along an upper surface of the flexible support sheet stabilizing the upward angle of the respective rib with respect to the support sheet.

16. The patient transport shield of claim 14, wherein pairs of the flexible ribs attach to each other over the flexible support sheet as they cross each other.

17. The patient transport shield of claim 1, wherein the set of flexible ribs are substantially flat in a relaxed state and wherein the set of flexible ribs are configured to flex to install the set of flexible ribs on the flexible support sheet in a manner that the ribs extend in an arch upward from the flexible support sheet and laterally across the flexible support sheet with ends of the arches attach to edges of the flexible support sheet.

18. The patient transport shield of claim 1, wherein the set of flexible ribs are inflatable tubular sleeves of flexible thermoplastic sheeting configured to provide stiffness while inflated while maintaining flexibility of the patient transport shield.

19. The patient transport shield of claim 1, wherein the set of flexible ribs are flexible polymer battens.

* * * * *